United States Patent [19]
Blunck et al.

[11] 3,949,231
[45] Apr. 6, 1976

[54] INFRARED RADIATING UNIT FOR INFRARED ANALYZERS

[75] Inventors: Otto Blunck, Hamburg; Heinz Delin, Wedel, Holst; Rudolf Müller, Hamburg; Werner Voss, Hamburg, all of Germany

[73] Assignee: H. Maihak A.G., Hamburg, Germany

[22] Filed: Apr. 10, 1975

[21] Appl. No.: 567,112

[30] Foreign Application Priority Data
Apr. 27, 1974 Germany............................ 2420545

[52] U.S. Cl.................................. 250/493; 350/294
[51] Int. Cl.².......................................... G21H 3/00
[58] Field of Search.................. 250/493, 495, 504; 350/293, 294; 240/41.35 R, 41.35 C

[56] References Cited
UNITED STATES PATENTS
2,275,745   3/1942   Eastman ............................ 250/504
3,325,629   6/1967   Shelby ............................... 250/493
3,445,662   5/1969   Langley ............................. 250/504
3,676,667   7/1972   Malifand ...................... 240/41.35 R

*Primary Examiner*—Archie R. Borchelt
*Assistant Examiner*—B. C. Anderson
*Attorney, Agent, or Firm*—Michael J. Striker

[57] ABSTRACT

A cylindrically shaped coil of resistance wire constitutes a source of infrared radiation which is located within a reflector comprised of a curved reflector section having a reflecting surface shaped to resemble an axially bisected rotationally symmetrical paraboloid, and a cylindrical reflector section which extends from an open side of the curved reflector section. The focal points of the reflecting surface are located on a circle which coincides with the outer circumference of the cylindrically shaped coil.

11 Claims, 2 Drawing Figures

INFRARED RADIATING UNIT FOR INFRARED ANALYZERS

BACKGROUND OF THE INVENTION

The present invention relates generally to an infrared radiator unit, and more particularly to an infrared radiator unit for infrared analyzers.

Infrared radiator units of this type are used in infrared analyzers and are electrically heated to approximately 1000K, so that the energy radiated by them is in the infrared portion of the spectrum.

When such units are used in infrared analyzers for measuring purposes, specific requirements are made of them with respect, inter alia, to the direction of the infrared radiation and the constancy of the emitted radiation, as well as with respect to the energy requirements of the source.

It is known that a particularly high effectiveness of the radiation utilized for measuring purposes can be obtained, if the infrared radiation which leaves the radiator unit issues in axially parallel condition, because this assures that the largest part of the radiation will enter axially parallel into the measuring or reference receptacle, rather than entering into it at an angle to impinge upon its side walls and become partly absorbed therein. To obtain this direction of the radiation it is known in the prior art to configurate the reflecting surface of the reflector of the unit as a paraboloid. However, the energy sources used in the art are not point sources but have an elongated configuration, so that a purely paraboloid-shaped reflecting surface does not adequately condense the radiation into a direct beam.

Another prior-art difficulty has been the very substantial influence of heat losses via the mountings of the energy source and the unit per se, upon the constancy of the radiation intensity. The better thermal conductivity there is between the energy source, the mount for the energy source and the housing, the more substantially the temperature of the energy source will be influenced by the ambient temperature, and this in turn leads to a wavelength shift in the major portion of the emitted radiation, so that the intensity of radiation is not constant.

Furthermore, it is desired that such infrared radiating units should require as little energy as possible for the operation, a condition which is particularly important if such units are employed in battery-operated infrared analyzers where the available battery energy is strictly limited.

Finally, another problem that has not been solved in the art is the mechanical stability of the mounting arrangement for the radiant energy source. If the source is shifted in any way in its position relative to the optical axis of the analyzer, by mechanical vibrations or the like, then the symmetry of the arrangement is disturbed and errors in measurement can and will occur.

SUMMARY OF THE INVENTION

Accordingly, it is an object of the present invention to provide an improved infrared radiating unit for infrared analyzers which overcomes the disadvantages of the prior art.

More particularly, it is an object of this invention to provide such an improved infrared radiating unit wherein the radiant energy is emitted largely in axial parallelism.

A further object of the invention is to provide such a unit which has a constant radiation output as a result of low heat losses.

In additional object of the invention is to provide such a unit which requires relatively little energy for its operation.

Still a further object of the invention is to provide a unit of the type in question wherein the energy source is mounted in such a manner as to be highly stable in its position relative to the optical axis, and in which the maintenance of thermal symmetry about the optical axis of the analyzer is assured even if the device undergoes exceptionally strong vibrations or other agitation.

In keeping with these objects, and with others which will become apparent hereafter, one feature of the invention resides in an infrared radiating unit for infrared analyzers which, briefly stated, comprises a cylindrically shaped source of infrared radiation, and a reflector partly surrounding the source and comprising a curved reflector section having a reflecting surface shaped to resemble an axially bisected rotationally symmetrical paraboloid, and a cylindrical reflector section extending from an open side of the curved reflector section. The focal points of the reflecting surface are located on a circle which coincides with the outer circumference of the cylindrically shaped source.

The present invention is thus characterized by a combination of features which assures its unique advantages and characteristics as compared to the prior art. These characteristics involve the configuration and material of the reflector, the manner in which the reflector is mounted, and the carrier for the source of radiation.

The reflector has a curved reflector portion, the reflector surface of which resembles an axially bisected rotationally symmetrical paraboloid which is pushed apart transversely of its bisection, and a cylindrical portion which extends from the curved portion of the reflector. The source of energy is a tubular coil or double coil of resistance wire having a cylindrical configuration, and the focal points of the individual cylinder-paraboloid sectors of the reflector surface are located on a circle which coincides with the circumference of this coil.

The reflector itself is produced of a material having a comparatively low coefficient of thermal conductivity, preferably a rust-resistant or rust-free steel which is known to have a comparatively low coefficient of thermal conductivity. The inner surface, that is the reflective surface of the reflector, is advantageously gold plated. The contact area between the reflector and the mount for the same is small so as to reduce the thermal-wedging effect, that is to reduce thermal conduction between them.

The carrier for the heating coil is of a ceramic material, and has a portion located outside the reflector and another portion which extends through an opening in the reflector into the interior thereof; this second portion has a smaller cross-sectional area than the remainder of the carrier. The latter is advantageously clamped in place, so that it can be shifted axially, can be turned about its longitudinal axis and can be replaced whenever desired or necessary.

The heating coil may be mounted on a metallic sleeve, preferably of rust-free steel, having axially spaced flanges between which the heating coil is located. This sleeve can then be pushed onto the smaller cross-sectional area portion of the carrier and can be secured thereon and placed in suitable manner, for example by means of an adhesive.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
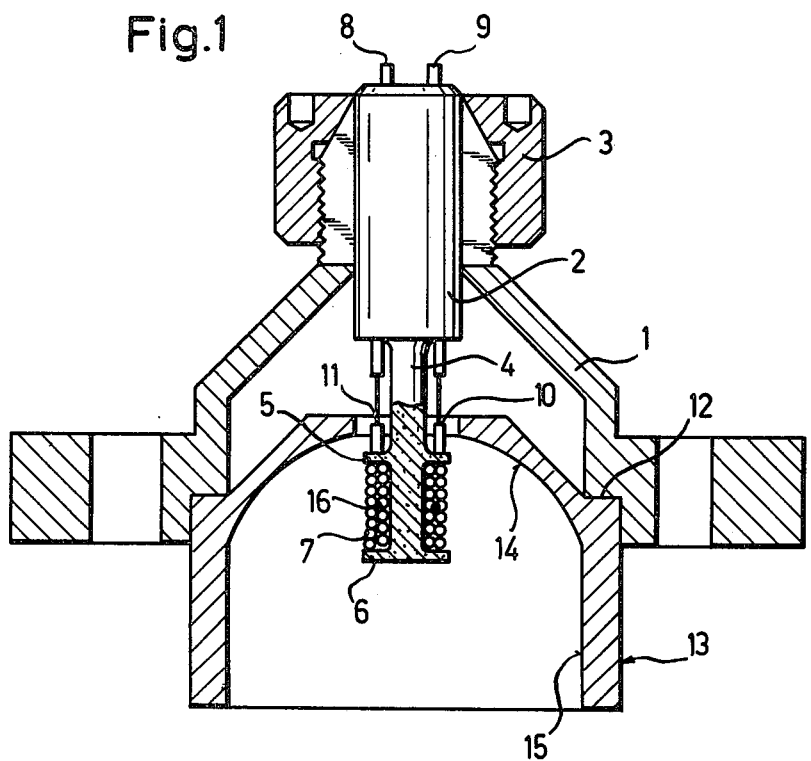
FIG. 1 is a somewhat diagrammatic axial section through a unit according to the present invention.

FIG. 1 shows an exemplary embodiment of an infrared radiating unit according to the present invention. This unit is to be used in an infrared analyzer of which the other components have not, however, been illustrated because they do not themselves form part of the invention. Such units in combination with infrared analyzers are of course well known.

The novel unit illustrated in FIG. 1 has a mount 1 another portion of which is formed with a central bore and is split along this bore; a carrier 2 of ceramic material has a larger-diameter portion which is located in this bore, and a nut 3 is threaded onto the exterior of the split upper portion of the mount 1 and pushes this portion, or rather the sections of this portion which result from the split, against the larger-diameter part of the carrier 2, thus clamping the same in such a manner that when the nut 3 is loosened, it can be shifted axially or turned. However, when the nut 3 is tightened, then the carrier 2 will be centrally and immovably clamped and held in place. The carrier 2 has a portion 4 of reduced cross-sectional area which extends out of the mount 1 and extends through an opening in a curved portion 14 of a reflector, from an open side of which curved portion there extends a cylindrical portion 13 of the reflector. The portion 4 is formed or provided with two axially spaced flanges 5 and 6 and carries intermediate these flanges a metal-jacketed resistance wire 7 formed as a coil which in the illustrated embodiment is configurated as a double-layer coil. The use of a double-layer coil produces a more homogeneous distribution of the infrared radiation. Within the metal jacket the resistance wire 7 is imbedded in a fire clay or the like, for example in magnesium oxide. Terminals 8 and 9 extend through bores in the carrier 2 to the reduced diameter portion 4 where they are hard-soldered to the wire 7a of the coil 7 and at the locations 10 and 11 where the wire 7a enters into the metal jacket of the coil 7 the open ends of the metal jacket are closed by pouring a ceramic substance into them which hardens and forms plugs.

The mount 1 is formed with a recess 12 in which the reflector 13 is secured, for example by a shrink fit. The reflector 13 has a central bore through which the portion 4 extends, and it is composed of the two parts 14 and 15 already mentioned. The inner reflector surface 14a of the part 14 is configurated as a rotationally symmetrical paraboloid which is axially bisected and pushed apart in transverse direction, so that the focal points 16 for the individual paraboloid sectors are located on a circle surrounding the axis of the arrangement, and which circle coincides with the circumference of the coil 7. This arrangement assures that the infrared radiation emitted from the middle of the coil 7 will, after reflection on the surface 14, be converted in axially parallel ways which increases the effectiveness of the unit since a larger proportion of the radiation than would otherwise be possible will now be passing through the measuring receptacle (not shown) to the radiation detector (not shown) of the infrared analyzer.

The reflector 13 is also of a material having relatively poor thermal conductivity, for example a rust-resistant steel having a high nickel content, or the like. The inner surface 14a of the portion 14, and if desired also the inner surface of the portion 15, can be polished and gold plated to obtain a particularly good reflection.

The unit of FIG. 1 has only small thermal losses due to its construction. The carrier 2 is of ceramic material having poor thermal conductivity, and in addition its portion 4 has a smaller cross-sectional area than the remainder of the carrier 2, so that the flow of thermal energy through the carrier 2 is further reduced thereby. The reflector 13 is heated by the heat of the coil 7, and due to the use of a material having poor thermal conductivity, for instance a rust-resistant steel having a small coefficient of thermal conductivity, the loss of heat by conduction to the mount 1 is maintained low. This effect is reinforced in that the contact area 12 between the mount 1 and the reflector 13 is relatively small.

The clamping of the carrier 2 between the arms formed in the mount 1 by the slot provided in the latter, and the clamping action exerted by the nut 3, mounts the carrier 2 centrically and in a very stable manner, so that it will not change its position relative to the optical axis of the arrangement even if the arrangement is subjected to exceptionately strong vibrations or the like. Moreover, this arrangement makes it possible for the carrier 2 and the coil 7 to be readily removed and replaced or inspected, and to be shifted axially or turned in order to select a position of the coil 7 in which a maximum yield and focussing of the radiation is obtained.

Figure 2:
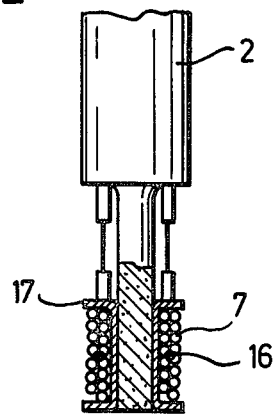
FIG. 2 is a fragmentary section illustrating a detail of a currently preferred embodiment.

The embodiment of FIG. 2 is in almost all respects identical with that of FIG. 1, so that the identical portions have not been illustrated. It differs from FIG. 1 in the manner in which the coil 7 is mounted on the carrier 2. For manufacturing reasons it is advisable not to mount the coil 7 directly upon the carrier 2, or rather the portion 4 thereof, since the carrier 2 would have to undergo mechanical stresses during the application of the coil and might break somewhere in its reduced cross-section portion 4. This problem is overcome in FIG. 2 by providing a metallic sleeve 17, again preferably of rust-resistant steel or the like, which is provided with axially spaced flanges or the like, and on which the coil 7 is mounted intermediate these flanges. The portion 4 then of course does not have similar flanges, and the dimension of the sleeve 17 is such that it can be pushed onto the portion 4 where it is secured in place, for example by means of an adhesive. This eliminates any mechanical stresses upon the carrier 2 and maintains all of the advantages outlined with respect to the description of FIG. 1.

The ceramic material for the carrier 2 consists of 99.9% pure $Al_2O_3$.

Instead of a rust-resistant steel as material for the mount 1 and the reflector 13 other materials having a relatively poor thermal conductivity may be used, for example Al$_2$O$_3$ ceramique or glass.

A suitable adhesive for securing the sleeve 17 in place on the portion 4 of the carrier is ceramic adhesive sold under the tradename "Thermoguss 2000".

An infrared analyzer in which the invention may be used is of the type as described in Luft U.S. Pat. No. 3,162,761.

It will be understood that each of the elements described above, or two or more together, may also find a useful application in other types of constructions differing from the types described above.

While the invention has been illustrated and described as embodied in an infrared radiator of unit for infrared analyzers, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An infrared radiating unit for infrared analyzers, comprising a cylindrically shaped source of infrared radiation; and a reflector partly surrounding said source and comprising a curved reflector section having a reflecting surface shaped to resemble an axially bisected rotationally symmetrical paraboloid, and a cylindrical reflector section extending from an open side of said curved reflector section, the focal points of the reflecting surface being located on a circle which coincides with the outer circumference of said cylindrically shaped source.

2. A unit as defined in claim 1, wherein said source is of hollow cylindrical configuration.

3. A unit as defined in claim 2, wherein said reflector is of rust-resistant steel.

4. A unit as defined in claim 2, wherein said reflector is of a material having a low coefficient of thermal conductivity.

5. A unit as defined in claim 2, wherein at least said reflecting surface is gold-plated.

6. A unit as defined in claim 2; further comprising a mount for said reflector, said mount engaging said reflector in a manner to reduce the conduction of thermal energy between them.

7. A unit as defined in claim 6; further comprising a carrier of ceramic material for said source; and wherein said source is a coil of resistance wire.

8. A unit as defined in claim 7, said carrier having a first portion outside said reflector, and a second reduced-diameter portion extending into said reflector and carrying said coil.

9. A unit as defined in claim 7; and further comprising clamping means replaceably clamping said carrier to said mount for axial and angular adjustment.

10. A unit as defined in claim 2; further comprising a carrier having at least a portion located within said reflector; said source comprising a metallic sleeve mounted on said portion and having axially spaced flanges, and a heating coil surrounding said sleeve intermediate said flanges.

11. A unit as defined in claim 10, wherein said sleeve is of rust-resistant steel.

* * * * *